United States Patent [19]

Gurchumelidze

[11] Patent Number: 5,512,045
[45] Date of Patent: Apr. 30, 1996

[54] SURGICAL DECOMPRESSION AND IRRIGATION APPARATUS AND METHOD

[76] Inventor: Teimuraz P. Gurchumelidze, 138 S. Johnson, Pontiac, Mich. 48341

[21] Appl. No.: 173,695

[22] Filed: Dec. 22, 1993

[51] Int. Cl.$^6$ ................................................ A61M 1/00
[52] U.S. Cl. ........................... 604/31; 604/35; 604/65
[58] Field of Search ....................... 604/27–32, 35, 604/43, 45, 65–67, 101, 248, 266, 270, 280

[56] References Cited

U.S. PATENT DOCUMENTS

| | | | |
|---|---|---|---|
| 1,607,726 | 11/1926 | Suszko | 604/32 |
| 1,973,845 | 9/1934 | Chenoweth | 604/32 |
| 2,148,541 | 2/1939 | Dierker | 604/35 |
| 2,854,982 | 10/1958 | Pagano | 604/101 |
| 3,091,239 | 5/1963 | Moeller | 604/67 |
| 3,593,713 | 7/1971 | Bogoff et al. | 604/27 |
| 3,823,714 | 7/1974 | Waysilk et al. | 604/28 |
| 3,982,535 | 9/1976 | Bahrton | 604/67 |
| 4,381,011 | 4/1983 | Somers . | |
| 4,465,482 | 8/1984 | Tittel . | |
| 4,631,054 | 12/1986 | Kim . | |
| 4,636,200 | 1/1987 | Vaillancourt . | |
| 4,642,092 | 2/1987 | Moss . | |
| 4,668,225 | 5/1987 | Russo et al. . | |
| 4,698,059 | 10/1987 | Johnson . | |
| 4,778,448 | 10/1988 | Meer . | |
| 4,801,294 | 1/1989 | Okada . | |
| 4,834,724 | 5/1989 | Geiss et al. . | |
| 4,834,725 | 5/1989 | Iwatschenko . | |
| 4,887,997 | 12/1989 | Okada . | |
| 4,902,276 | 2/1990 | Zakko | 604/28 |
| 5,078,701 | 1/1992 | Grassi et al. . | |
| 5,078,702 | 1/1992 | Pomeranz . | |
| 5,152,756 | 10/1992 | Quinn et al. . | |
| 5,178,606 | 1/1993 | Ognier et al. | 604/31 |
| 5,242,404 | 9/1993 | Conlex et al. | 604/30 |
| 5,273,523 | 12/1993 | Sozuki et al. | 604/28 |

*Primary Examiner*—C. Fred Rosenbaum
*Assistant Examiner*—Frank Wilkens, III
*Attorney, Agent, or Firm*—Brooks & Kushman

[57] ABSTRACT

An apparatus (10) and method for surgical decompression and irrigation/lavage of a patient comprising a tube (12) having a distal end (14) which is inserted into the intestine and a proximal end (16) which is located outside the patient. The tube (12) has a wall which surrounds a plurality of longitudinally extending lumens. A suction lumen (22) is connected to a suction means located exteriorly in relation to the patient. There are one or more pores capable of delivering irrigation fluid and for syphoning the contents of the patient's intestine. An irrigation lumen (24) is connected to irrigation means (32) located exteriorly in relation to the patient. There are one or more openings extending from the suction lumen (22) to the irrigation lumen (24) for ducting irrigation fluid or gastrointestinal content and for avoiding plugging of the pores by particulate matter or by a stomach lining when the stomach is aspirated.

29 Claims, 3 Drawing Sheets

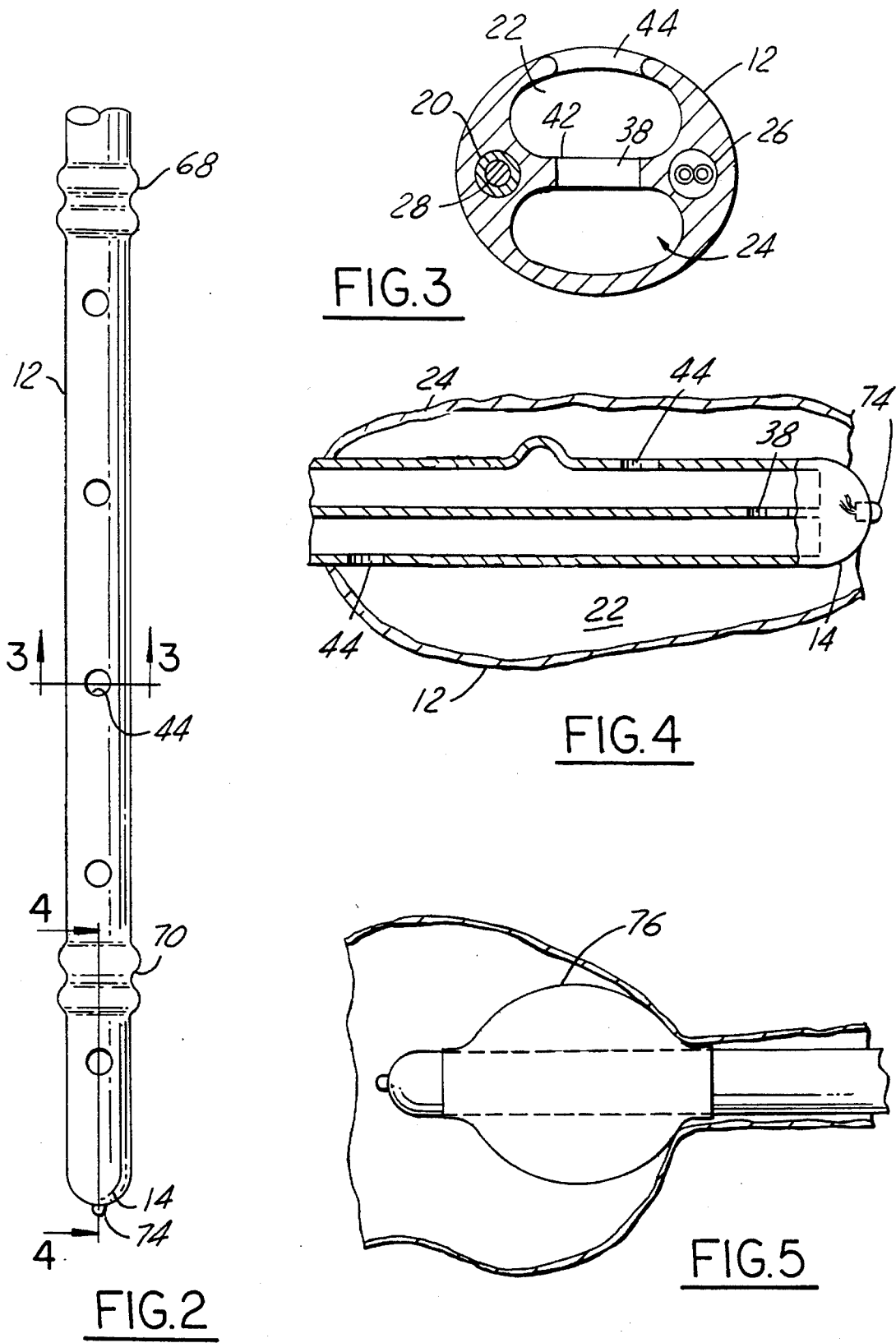

SURGICAL DECOMPRESSION AND IRRIGATION APPARATUS AND METHOD

BACKGROUND

1. Field Of The Invention

The present invention is related to surgical suction and irrigation/lavage apparatus and methods, in particular those used for intraoperative gastric and bowel decompression to alleviate distension when the bowel is obstructed.

2. Related Art

Intestinal decompression has become an important procedure in abdominal surgery. In patients with small bowel obstruction (due to adhesions, tumors, hernias, etc.) and paralytic ileus there is an accumulation of ingested fluid, secretions and intestinal gas within the gastrointestinal tract. These produce distention of the intestine. Because of intestinal stasis, rapid intraluminal bacterial proliferation occurs. Normally, the small intestine contains very small quantities of bacteria and may be almost sterile. This distention and stasis has a profound effect on surgical results.

Any violation of bowel integrity significantly increases the likelihood of a postoperative intra-abdominal and wound infection due to the high risk of intra-operative contamination with postoperative enteric or anastomotic leak.

Bowel distention and increased intraluminal pressure inevitably impairs circulation to the bowel. This vascular compromise, along with intraluminal contamination can disrupt healing anastomoses and may lead to peritonitis.

The intraluminal fluid which contains toxic material is absorbed from the gastrointestinal tract. This produces systemic effects. Patients with intestinal distention have a high risk of postoperative motility disorders and prolonged post-operative ileus which greatly worsens the post-operative prognosis.

In patients with a distended bowel, intraoperative manipulations and abdominal closure are greatly impeded. In these patients it is essential to decompress the distended bowel to prevent intra-operative and post-operative complications. There is general consensus that in the surgical management of bowel obstruction, distention of the intestine requires proper attention.

Decompression of the bowel may be performed via enterotomy (open) or by "closed" techniques. Open methods entail the performance of enterotomy and/or enterostomy. Such techniques carry a high risk of intra-operative contamination in the abdominal cavity and the ability to perform adequate decompression throughout the obstructed bowel is effectively limited to the proximity of the "opened" areas only. "Closed" methods of decompression are carried out without violation of bowel integrity and require insertion of the intestinal tube into the gastrointestinal tract transnasally, orally, or through the anal canal.

The use of different catheters for nasointestinal decompression has long been known in the prior art. Some tubes are designed to be emplaced into the small bowel during the surgery and are provided with pairs of inflatable balloons which facilitate the manual manipulation of the catheter through the small intestine. C. Grassi, U.S. Pat. No. 5,078,701, describes an intestinal catheter which may be inserted into the gastrointestinal tract by use of a guide wire without surgery. A tip opening is connected to a feeding lumen and allows nutritive material to flow into the small intestine. Gastric openings located near the middle of the catheter and connected to the suction lumen permit aspiration of gastric content.

Such tubes are somewhat effective in carrying out intestinal decompression in pre-operative and post-operative periods. However, there is often a need to perform rapid and effective bowel decompression during surgery. Existing tubes fail to intubate the gastrointestinal tract effectively during surgery.

The gastrointestinal tract comprises the mouth, the esophagus, the duodenum, the small intestine and the large intestine. The gastroduodenal part of the gastrointestinal tract contains several regions of angulation and curvature. The pyloric part of the stomach contains a thick layer of muscles which are aggregated into the annular pyloric sphincter that contracts intermittently. The duodenum is curved in an incomplete circle and frequently shows variations in configuration. These portions of the gastrointestinal tract have traditionally been considered to be difficult to negotiate and frequently lead to technical difficulties and failure to emplace the tube into the small bowel.

Existing tubes are subject to frequent coiling and kinking, which create difficulties in manipulation and require of the surgeon special skill and dexterity. Even when the tube is emplaced in the small bowel, the construction and technical properties of currently available tubes do not allow a loaded small bowel to be cleansed to a desirable degree. Specifically, their small internal diameters have small suction openings and hence reduced cross-sectional areas that prohibit effective decompression within a reasonable time and do not avoid tube plugging by the bowel wall, or clogging and obstruction by the bowel wall and enteric content.

Existing medical suction devices (aspirators) are of two types: (1) continuous, and (2) intermittent. Continuous suction devices often become plugged with debris and organ tissues, causing inefficient evacuation of gas and fluid. Intermittent suction devices are regulated by thermotic or timing valves which shut off a suctioning phase and/or turn on an injection phase. Both methods of suctioning frequently fail to work satisfactorily. Timing valves shut off the suctioning phase after a pre-set time. Such systems cut off suction even when cessation is not required. Conventional systems may occlude after a certain period of time regardless of any other factors, such as intrinsic pressure. There is a need for a device which temporarily arrests suction only when the organ, cavity or space which needs to be decompressed, is empty and irrigates or vents the tube automatically only when there is a demand and effectively prevents an obstruction of the tube between the decompressed space and the suction device. If suction were to continue at that point, patients may develop serious or life-threatening complications.

SUMMARY OF THE INVENTION

A general object of this invention is to provide an improved surgical method for intubation of gastrointestinal organs which require decompression, irrigation, or both.

More specifically, an object of the present invention is to provide a tube which allows easy and rapid emplacement into the small bowel. The tube allows fast and effective intra-operative decompression and irrigation of the small bowel. The tube can be inserted into the small bowel during the surgery orally or transnasally and removed after the decompression is achieved.

The tube comprises a long, quadruple lumen catheter with a circular cross-section. A first lumen provides suction. A second lumen vents the suction lumen and is a conduit for an irrigation/lavage solution. A third lumen serves as a conduit for an embodied spring wire for preventing kinking and controlling the tube's rigidity. A fourth lumen ducts wires for illumination and transmission of pressure signals.

Connected to the tube is an improved suctioning system. The system maintains intermittent suctioning based on intrinsic pressure changes within the system as the demand requires. The apparatus also allows irrigation of the tube without disconnection. Intermittent suctioning is regulated by a self-controlled, feedback-oriented pressure-dependent manometric device.

BRIEF DESCRIPTION OF THE DRAWINGS

FIG. 2 is a perspective view of an embodiment of the present invention, illustrating a pair of contoured surfaces located proximate a distal end of the tube which facilitates kneading the bowel over the tube;

FIG. 3 is a cross-sectional view of the tube taken along the line 3—3 of FIG. 2;

FIG. 4 is a sectional view of the distal end of the tube taken along the line 4—4 Of FIG. 2;

FIG. 5 iS a cross-sectional view of the distal end of the tube, illustrating an outer sheath and an inflated balloon located at the gastro-esophageal junction to prevent regurgitation.

DETAILED DESCRIPTION OF THE PREFERRED EMBODIMENTS

Figure 1:
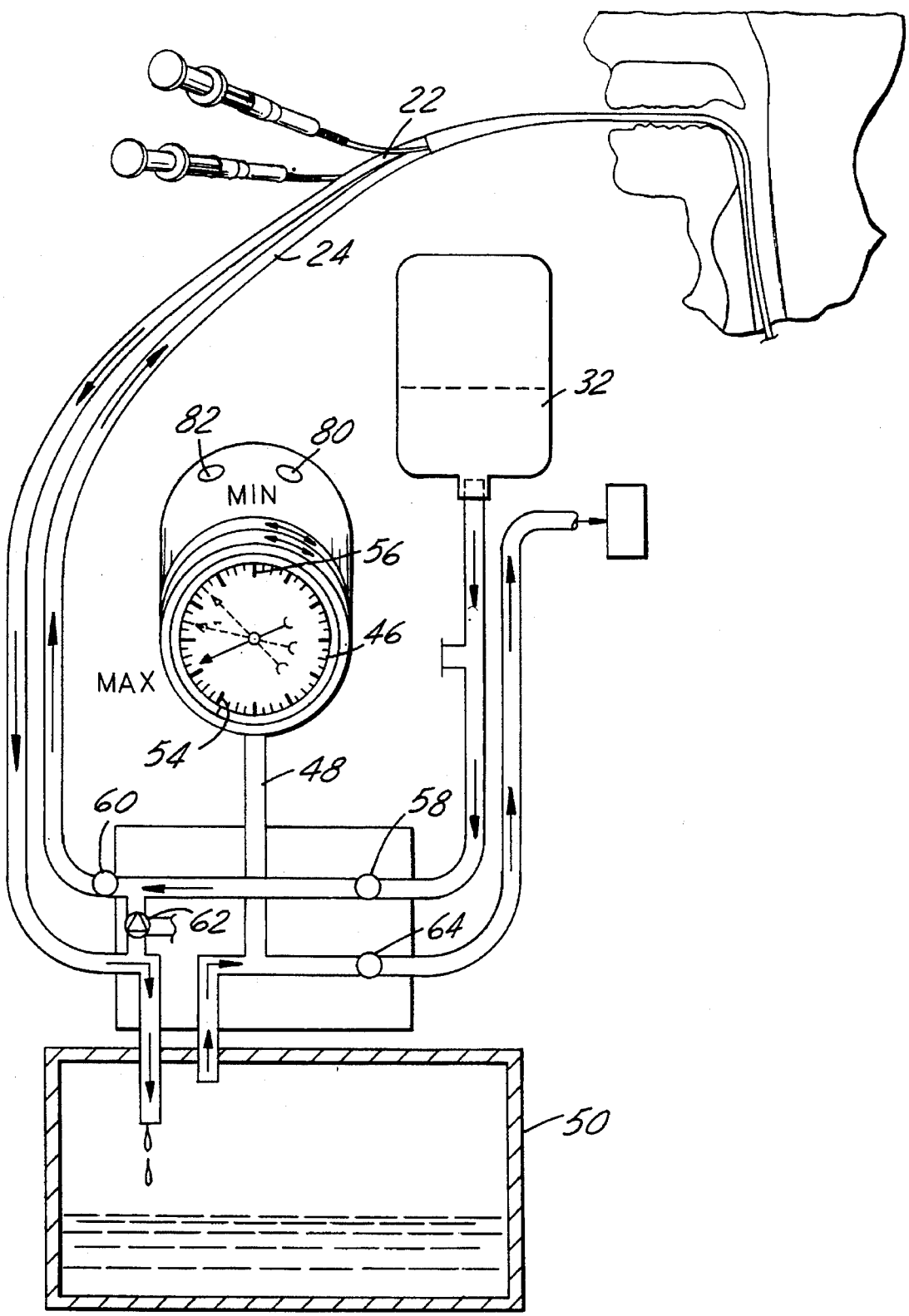
FIG. 1 is a system flow diagram illustrating instrumentation, including a manometric device, which is connected to a tube of the present invention.
Figure 6:
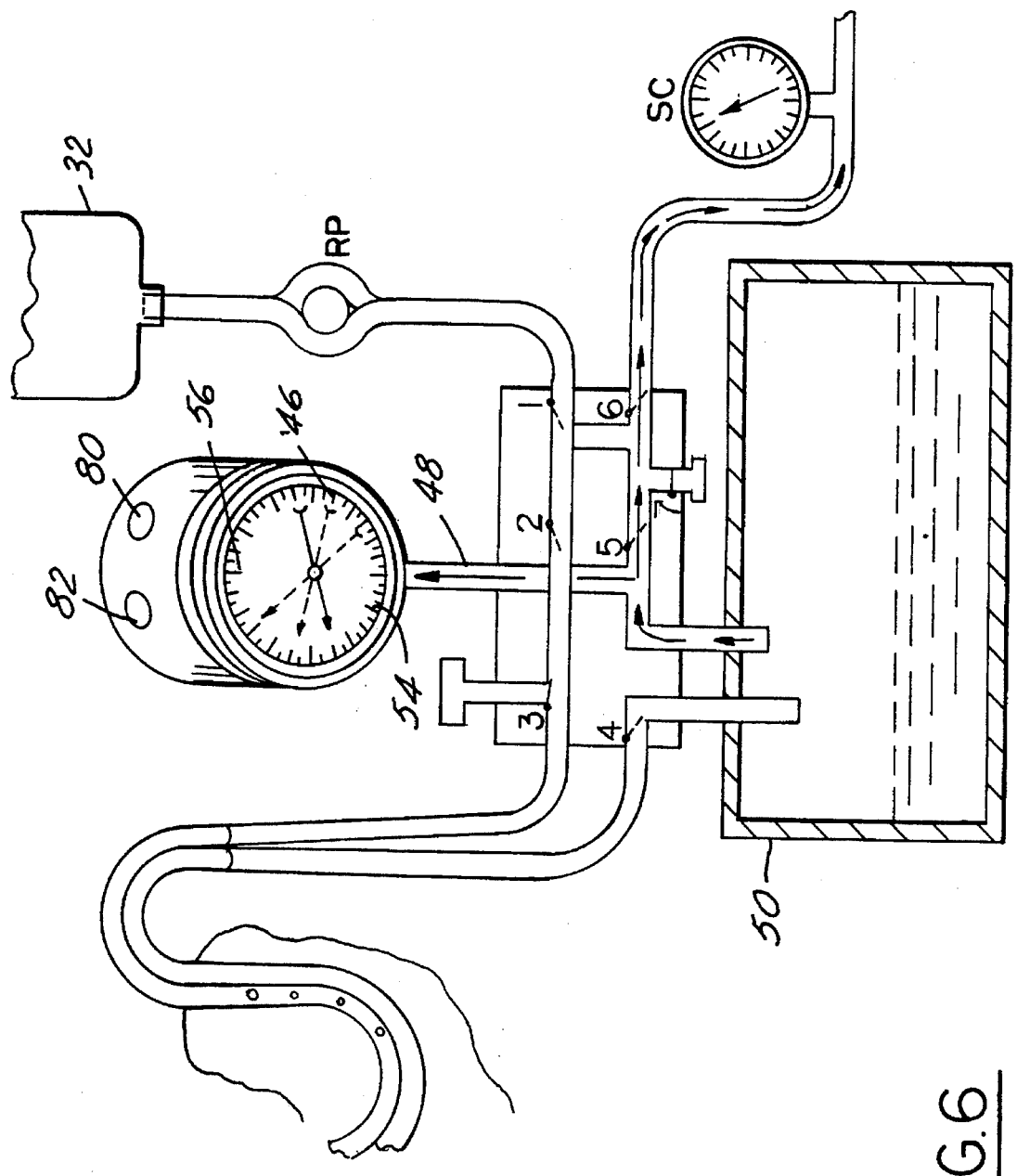
FIG. 6 depicts an alternate embodiment of the invention, illustrating interconnections and valve configurations which permit the system to be used in any of nine modes of operation.

Turning first to FIGS. 1 through 6 of the drawings, there is depicted an apparatus 10 for surgical, or gastrointestinal decompression and irrigation of a patient. The apparatus includes a tube 12 with a distal end 14 which is inserted into the intestine through the nasal or oral orifice. If there is a need for large bowel decompression, it can be inserted through the anal canal or through enterotomy. A proximal end 18 is located outside the patient. Having a generally circular cross-section, the tube 12 defines quadruple longitudinally extending lumens 20, 22, 24, 26 (FIG. 3).

Accommodated within a guide wire lumen 20 is a spring wire 28 which prevents kinking of the tube 12 during insertion into the patient and for stiffening the tube, thereby facilitating emplacement in the gastrointestinal tract. A spring wire 28 may be of any kind which has a stiffening means. Exemplary of such means include intermeshing coils which stiffen the spring wire 28 upon squeezing.

Suction means 30, such as a vacuum pump (FIG. 1), are connected to the suction lumen 22 via a container 50 for receiving syphoned fluid. Irrigation means, such as a fluid delivery device 32, are connected to an irrigation lumen 24.

If desired, an electrical supply means (not shown) is in electrical communication with a lamp 74 (FIG. 2) along the electrical lumen 26, so that signals are communicated from a pressure sensing device located at the distal end 14 of the tube 12, and so that the lamp 74 may be illuminated if desired.

One or more openings 38 extend through a septum 42 of the tube 12 (FIG. 4) from the suction lumen 22 to the irrigation lumen 24 for ducting irrigation fluid or gastrointestinal content from the irrigation lumen 24 to the suction lumen 22 and for venting the suction lumen in case the pores 44 are plugged by solid matter or by the stomach lining.

To communicate negative pressure to gastrointestinal contents or other spaces which require decompression, the suction pores 44 extend laterally from the suction lumen 22 through an outside wall of the tube 10.

Referring now to FIG. 1, the apparatus of the invention comprises suction lumen 22, a manometric device 46 with an inflow channel 48 and a container 50 for fluid collection. The manometric device 46 is located between a centralized suction system 30 and the sealed container 50. The manometric system has an indicator 52, which indicates pressure and first and second pre-set stops or electrodes 54, 56. If desired, the indicator 52 may have its oscillation damped by a suitable vibration dampening means.

The system works in the following manner. When the negative pressure (suction) is applied to the suctioning lumen, negative pressure gradually builds in the organ, cavity or space (closed system). As negative pressure in the system builds, the indicator 52 moves towards the first electrode 56. As pressure in the inflow channel 48 falls due to the negative pressure, the indicator 52 contacts the electrode 56. At that moment, the suction control valve 64 will cut off the suction system 30. Other valves, 58, 60, 62, will control the air vent and fluid flow of the irrigation solution. Air and/or saline solution, or both, will gradually enter the system, and the negative pressure will become alleviated. At that time the indicator will move in the opposite direction (towards second electrode 54) and finally will contact the electrode located thereat.

Then, the pressure in the decompressed organ or cavity will approximate the pre-set maximum level. Contact with electrode 54 will close valves 58, 60, 62 so that no more air or fluid may enter the organ cavity. At that moment, the suction system becomes on-line via valve 64, and the pressure begins to fall, moving the indicator again towards 56. This movement of the indicator back and forth will continue intermittently. In practice, the manometric device 56 is in electrical communication with the valves 58, 60, 62, 64. Further detail of the operating modes 1–9 are to be discussed later.

The system also permits increasing or decreasing pressure in the system by moving the pre-set pressure levels 54, 56 towards each other or apart. This is achieved by moving the electrodes clockwise or counterclockwise with a suitable means, such as two rotary rings inset into the manometric device (FIG. 1).

Referring again to FIG. 1, to assist the surgeon in using the disclosed system, there are provided visual or aural phase indicators 80, 82. For example, indicator 80 may usually take the form of a red lamp, while 82 may be a violet-colored lamp, if desired. The chart below summarizes the indications during suction, transition from suction to irrigation, irrigation, and suction phases of the disclosed apparatus:

| Phase | Phase Indicator | | Needle Movement |
| --- | --- | --- | --- |
| | Violet (80) | Red (82) | |
| Suction | ON | OFF | Clockwise |
| Suction/ Irrigation | OFF | ON | Static |

| Phase | Phase Indicator | | Needle Movement |
| --- | --- | --- | --- |
| | Violet (80) | Red (82) | |
| Irrigation | OFF | ON | Counter-clockwise |
| Suction | ON | OFF | Static |

Disclosure will now be made of the surgical procedures by which the apparatus 10 of the present invention may be used.

The main steps are as follows:

Insert the tube 12 within a sheath 66 (FIG. 5);

2. Intubate the patient in a routine manner;

3. Inflate a balloon 76 via an inflation channel 78 which is located outside and extends along the length of the sheath 66;

4. Withdraw the sheath 66, leaving the tube in place so that the balloon 76 blocks the gastroesophageal junction to prevent regurgitation of the gastrointestinal contents while carrying out the procedure (FIG. 5);

5. Advance the tube toward the pylorus and to the duodenum through the curvatures of the duodenum and the small bowel. During this step, the flexibility of the tube may be changed by altering the stiffness of the guidewire;

6. Transillumination can be used in order to properly locate the distal end of the tube in the duodenum and to direct the tube to the small bowel. In this step, a source of illumination 74 located at the distal end 14 of the tube 12 is energized;

7. Grasp or knead through the bowel the tube thereby advancing the tube further into the bowel to the desired extent;

8. Connect the apparatus 10 to an external system (FIG. 1);

9. Decompress or syphon off the bowel contents and irrigate until the effluent is clear or reduced;

10. Remove the tube slowly while continually decompressing the small bowel, duodenum, and stomach;

11. Totally decompress the stomach so that no residual content can be regurgitated;

12. Remove the tube further;

13. Deflate the balloon and remove the sheath with the balloon.

It should be noted that the above described decompressive and irrigation procedure can be performed with any environment requiring drainage and/or decompression, e.g. the sump drains placed in the cavity of a wound or abscess. For general surgical applications, less than all of the four lumens may be needed. For example, the spring wire lumen 28 may not be needed. Nor may the electrical supply lumen 26 be required, so that only two lumens, irrigation and suction may be in operation.

Medical drainage system can broadly be classified as "closed suction" and sump drains. In closed suction drainage systems, there is one lumen, which drains a closed system. As a result, the system tends to collapse under the influence of the vacuum created thereby and tends to become sealed. In sump drainage systems, however, there are generally two lumens. One provides drainage, while another provides venting. In such systems, no appreciable vacuum is formed. The present system can be utilized with different drainage systems. If closed, a suction draining technique is used, e.g. in pleural space drains, only with one lumen chest tube. To define a suitable suctioning regime, the indicator would be placed in a pre-set negative pressure by regulating the suction vent 30. If the pressure in the suction tube drops, the arrow will move towards preset minimum pressure considered to be critical. Ultimately, the arrow will touch the contact (54) and the (red) lamp 80 will illuminate. Simultaneously, a timer will turn on. If the negative pressure in the system does not start building up after the pre-set period of time, an emergency alarm may provide a cue to decrease pressure in the system.

The 3-way stopcock valve 62 allows fluid communication between the irrigation and suction lines. In one valve configuration there is flow between the suction line and ambient air. In another there is fluid communication between the irrigation line and ambient air. Thus, by suitable orientation of the valve 62, the irrigation fluid may flow alone, air may flow alone, or the irrigation fluid and air may flow together toward the closed system 72.

The different modes in which the disclosed apparatus can be used will be described.

Mode 1—Standstill

In this mode, all valves are closed. No drainage occurs, and there is no air or fluid inflow;

Mode 2—Passive Drainage

In this mode, the irrigation and suction lumens function, but passively under ambient atmospheric pressure. Outflow of, for example, stomach contents, occurs solely under the influence of gravity;

Mode 3—Filling-Slow Inflow

In this mode, there is a slow inflow of irrigation solution into the stomach or cavity to be treated. In this mode, the disclosed apparatus is used to administer a medicament to the vessel to be treated;

Mode 4—Passive Irrigation

In this mode, both the inflow of irrigation fluid and the outflow of, for example, stomach contents, occurs solely under the influence of gravity. There is no communication of negative pressure by the suctioning system;

Mode 5—Active Irrigation

In this mode, a positive pressure means, such as a roller pump, is in fluid communication with a source of irrigation fluid. Inflow occurs under the positive pressure which is used in part to displace fluid in the vessel to be treated so that it emerges into a collecting container. Again, no negative pressure is communicated to the vessel to be treated by a central suctioning system;

Mode 6—Active Simultaneous Suction-Irrigation

In this mode, there is negative pressure communicated by the central source thereof to the container and to the manometric device. Simultaneously, active irrigation of the space which requires decompression and/or lavage of the organ or space is carrout out;

Mode 7—Intermittent Pressure Dependent Suction-Irrigation

Step 1—Suction

In step 1 of this mode, suction is applied, the irrigating fluid is turned off, and pressure in the system declines, as registered by a clockwise movement of the indicator in the manometric device;

Step 2—Suction-Irrigation Transition

In this configuration, pressure in the vessel to be decompressed diminishes and reaches a minimum level. At this point, the arrow of the manometric device moves and touches the contact 56. Suction is then arrested and the illuminated indicator 80 activates. Irrigation then begins and pressure in the system begins accumulating. At that moment, irrigation occurs under the influence of existing negative pressure, gravitational forces, and the elastic forces exerted by a decompressed organ as it tends to revert to its original, compliant shape;

Step 3—Irrigation

In this configuration, the indicator of the manometric device slowly moves counterclockwise as negative pressure in the system continues to be alleviated.

Step 4—Suction

In this configuration, suction predominates, and the vessel to be treated begins to be evacuated;

Mode 8—Sump Suction

In this configuration, the device is being used as a sump, wherein an air vent and suction combine to promote free drainage or purging of the vessel to be treated;

Mode 9—Closed Suction

In this mode, the supply of irrigation fluid is isolated, and the vessel to be treated becomes contracted; and Mode 9—Violated Closed Suction In this configuration, if the seal formed by the vessel to be treated breaks, e.g. there is an air leak from a lung, the arrow in the manometric device will inevitably turn counterclockwise and touch the contact 54. An alarm will sound at this point, indicating a potentially dangerous condition.

FIG. 4 is an enlarged sectional view of the distal end 14 of the tube 12. As will now be apparent, the manometric device 46 enables negative pressure to be applied in a pulsating manner. In one cycle, suction is applied, while in the subsequent cycle, suction is suppressed. Under gravity, or under externally applied pressure, the irrigation fluid travels along the irrigation lumen 24 and emerges from the tube 12 at its distal end 14 through pores 38. The stomach lining 72 envelopes the distal end 14 of the tube 12, forming a closed system. When suction is applied, the gastrointestinal contents are syphoned through the pores 38 and through the gate 44, before being transported along the suction lumen 22. If solid matter or the stomach lining plugs or blocks any pore 38, fluid communication is still enabled via other pores 38 and the gate 44.

Continuing with reference to FIG. 4, in the disclosed configuration, there is a solution to problems which were manifest in prior art approaches. Under traditional approaches, plugging of a pore 38 often resulted in an absence of flow. It was not always clear to the surgeon as to why flow had stopped. A question may have lingered as to whether the absence was attributable to the absence of stomach content (decompression complete) or to obstruction by food particles, blood clots, or other materials (decompression incomplete). In contrast, the tube and associated apparatus of the present invention allow suction and flow to continue intermittently.

The tube can be produced from silicon as well as other elastic natural or artificial (synthetic) materials. The manometric device 56 of the present invention can usefully be embodied in an intermittent suction unit, such as that sold by the BOC Health Care Company (OHMEDA model), or the Boehringer Company's intermitting suction regulator (Model 7702).

Noteworthy is that the present invention discloses a system which is driven in response to the pressure sensed by the manometric device 56. This is an indicator of pressure existing within the closed system 72 (FIG. 4). So that such pressure is sensed directly, none of the pores 38 may lie outside the closed system 72.

Continuing with reference to FIG. 4, the distal end 14 may include a tip structure which includes a pressure transducer connected to an external pressure gauge independent of the manometric device 56. Such a pressure gauge is helpful in corroborating data indicated by the device 56 and may, in an emergency case or if desired, be used to override the pulsating influence of the device 56. Although not depicted, it will be apparent to those of ordinary skill that there is a means for communicating to each of the valves a suitable electrical signal for triggering their opening and closing in response to pressure sensed in the inlet channel 48.

Having above indicated a preferred embodiment of the present invention, it will occur to those skilled in the art that modifications and alternatives can be practiced within the spirit of the invention. It is accordingly intended to define the scope of the invention only as indicated in the following claims.

What is claimed is:

1. An apparatus for surgical decompression and irrigation of a patient comprising:

a tube having a distal end which is inserted into a body cavity, the tube having a proximal end which is located outside the patient, the tube having a wall which surrounds a plurality of longitudinally extending lumens;

a suction lumen connected to a suction means located exteriorly in relation to the patient;

one or more pores extending laterally through the wall of the tube capable of delivering irrigation fluid, for syphoning the contents of the patient's cavity;

an irrigation lumen connected to irrigation means located exteriorly in relation to the patient;

one or more openings extending from the suction lumen to the irrigation lumen for ducting irrigation fluid or the contents of the cavity to be drained, and for avoiding plugging of the apparatus by particulate matter or by a cavity lining when the cavity is being aspirated; and a manometric device in communication with the suction means, the manometric device having a pressure indicator and first and second pre-set stops for maintaining intermittent vacuum build-up and relief, the manometric device being in fluid communication with a suction system and a container, the indicator moving in response to vacuum sensed within an inflow channel which is in fluid communication with the bowel or other organ.

2. The apparatus of claim 1 further comprising suction connection means for connecting the suction lumen to the suction means.

3. The apparatus of claim 1 further comprising irrigation connection means for connecting the irrigation means to the irrigation lumen.

4. The apparatus of claim 1 wherein the one or more openings comprise one opening.

5. The apparatus of claim 1 wherein the suction lumen and the suction means are in fluid communication with a container which collects the contents of the bowel or other organ and irrigation solution syphoned from the patient.

6. The apparatus of claim 1 wherein the manometric device is located between a centralized suction system and a container, the manometric device having an indicator which moves in response to pressure sensed within an inflow channel which is in fluid communication with the bowel or other organ.

7. The apparatus of claim 1 further comprising an air vent in communication with the irrigation means.

8. An apparatus for gastrointestinal decompression and irrigation of a patient comprising:

a tube having a distal end which is inserted into the intestine and a proximal end which is located outside the patient, the tube having a wall which surrounds a plurality of longitudinally extending lumens;

a guide wire lumen for housing a guide wire having an attribute of changeable flexibility to assist in advancing the tube, the guidewire preventing kinking of the tube during insertion into the patient and for stiffening the tube;

a suction lumen connected to a suction means located exteriorly in relation to the patient;

one or more pores extending laterally through the wall of the tube, capable of delivering irrigation fluid and for syphoning the contents of the patient's intestine;

an irrigation lumen connected to an irrigation reservoir for delivering the irrigation fluid to the one or more pores;

an electrical lumen in communication with an electrical supply means; and one or more suction openings extending from the suction lumen to the irrigation lumen for ducting irrigation fluid or gastrointestinal content and for avoiding plugging of the pores by particulate matter or by a stomach lining when the stomach is aspirated.

9. The apparatus of claim 1 further including a sheath for receiving the tube.

10. The apparatus of claim 9 further including a balloon which extends circumferentially around an outside surface of the sheath, the balloon being capable of being seated at the gastro-esophageal junction to prevent regurgitation of the stomach contends.

11. The apparatus of claim 1, wherein the manometric device further includes a vibration dampening means for reducing oscillation of the pressure indicator and for resisting abrupt pressure changes.

12. The apparatus of claim 11, wherein the pressure indicator moves toward the first stop as negative pressure in the suctioning lumen builds.

13. The apparatus of claim 12, further including a suction control valve in communication with the suction system and operable in response to the manometric device, the valve cutting off the suction system when the pressure indicator contacts the first stop.

14. The apparatus of claim 13, further including an air vent valve and a fluid flow valve operable in response to the manometric device, the negative pressure becoming alleviated as air and/or a fluid enters the apparatus, the pressure indicator then moving in an opposite direction toward the second stop until contact therewith, the pressure in the decompressed organ or cavity then approximating a pre-set maximum level indicated by the second stop.

15. The apparatus of claim 14, wherein the air vent and fluid flow valves are closed upon contact of the pressure indicator with the second stop, thereby reintroducing the suction system to the apparatus so that pressure may again fall and the pressure indicator may move toward the first electrode.

16. The apparatus of claim 15, wherein the pressure indicator may move back and forth intermittently between the stops, the apparatus thereby permitting increasing or decreasing pressure in the system by moving the pre-set stops in relation to each other by clockwise or counter clockwise means for moving.

17. An apparatus for surgical decompression and irrigation of a patient comprising:

a tube having a distal end which is inserted into a body cavity, the tube having a proximal end which is located outside the patient, the tube having a wall which surrounds a plurality of longtitudinally extending lumens;

a suction lumen connected to a suction means located exteriorly in relation to the patient;

one or more pores extending laterally through the wall of the tube capable of delivering irrigation fluid, for syphoning the contents of the patient's cavity;

an irrigation lumen connected to irrigation means located exteriorly in relation to the patient;

one or more openings extending from the suction lumen to the irrigation lumen for ducting irrigation fluid or the contents of the cavity to be drained, and for avoiding plugging of the apparatus by particulate matter or by a cavity lining when the cavity is being aspirated;

a manometric device in communication with the suction means, the manometric device having a vacuum indicator and first and second pre-set stops for maintaining intermittent vacuum buildup and relief;

a suction control valve in communication with the suction means, the valve cutting off the suction means when the vacuum indicator contacts the first stop;

an air vent valve and a fluid flow valve operable in response to the manometric device, the suction becoming alleviated as air and/or a fluid enters the apparatus, the vacuum indicator then moving in an opposite direction toward the second stop until contact therewith, the vacuum in the decompressed organ or cavity then approximating a pre-set maximum level indicated by the second stop;

the air vent and fluid flow valves then being closed upon contact of the indicator with the second stop, thereby reintroducing the suction means to the apparatus so that vacuum may again fall and the indicator may move toward the first electrode;

the vacuum indicator being able to move back and forth intermittently between the stops, the apparatus thereby permitting increasing or decreasing vacuum in the system by moving the pre-set stops in relation to each other by clockwise or counter-clockwise means for moving, wherein the means for moving comprise a rotary ring associated with each stop, thereby allowing the presetting of a range of vacuum boundaries arbitrarily.

18. The apparatus of claim 17, further comprising phase indicators which signify suction, transition from suction to irrigation, and irrigation modes of the apparatus.

19. The apparatus of claim 18, wherein the phase indicators are visual indicators.

20. The apparatus of claim 18, wherein the phase indicators are aural indicators.

21. An apparatus for surgical decompression and irrigation of a patient's bodily organ or cavity comprising:

a suction means including a first suction conduit fluidly communicating with a suction line of a catheter placed in the patient's organ or cavity;

a container for collecting material;

a second suction conduit fluidly communicating between the container and a suction source;

a vacuum sensor for detecting a level of negative pressure; and a vacuum controller-indicator, whereby when the vacuum is applied to the second conduit, a vacuum condition is generated in the second suction conduit and conveyed to the container which is hermetically isolated from ambient atmosphere and fluidly communicated with the second suction conduit, so that any pressure/vacuum change in the patient's organ or cavity or applied vacuum level will cause consequential changes in the pressure level in the first suction conduit, the container, and the second suction conduit;

wherein a vacuum change in either suction conduit or suction source or the reservoir communicates a signal to the vacuum controller-indicator so that the vacuum condition can be maintained in isolation from the vacuum source, thereby avoiding continuous operation of a pump motor connected to the vacuum source.

22. An apparatus for surgical decompression and irrigation of a patient's bodily organ or cavity comprising:

a suction means including a first suction conduit fluidly communicating with a suction line of a catheter placed in the patient's organ or cavity;

a container for collecting material;

a second suction conduit fluidly communicating between the container and a suction source;

a vacuum sensor for detecting a level of negative pressure; and a vacuum controller-indicator, whereby when the vacuum is applied to the second conduit, a vacuum condition is generated in the second suction conduit and conveyed to the container which is hermetically isolated from ambient atmosphere and fluidly communicated with the second suction conduit, so that any pressure/vacuum change in the patient's organ or cavity or applied vacuum level will cause consequential changes in the pressure level in the first suction conduit, the container, and the second suction conduit;

wherein a vacuum change in either suction conduit or suction source or the reservoir communicates a signal to the vacuum controller-indicator so that the vacuum condition can be maintained in isolation from the vacuum source, thereby avoiding continuous operation of a pump motor connected to the vacuum source;

wherein the vacuum controller-indicator is in communication with the vacuum sensor;

the vacuum controller being represented as a manometric device having an arrow which moves rotationally in response to vacuum sensed within the suction means;

the direction of rotational movement of the arrow being determined by the vacuum condition in the suction means, so that the arrow moves in one direction when the vacuum in the suction means builds and moves in the opposite direction as the vacuum in the suction means is alleviated;

wherein the arrow is communicated with a vibration dampening means for reducing oscillations of the indicator and for resisting abrupt pressure changes within the suction means;

wherein the manometric device of the vacuum controller has mounted rotary rings capable of sliding clockwise and counter-clockwise;

a first rotary ring being associated with a first stop-electrode, so that the rotational movement of the said first ring will result in a rotational movement of the first stop-electrode, thereby pre-setting the level of a desired maximum vacuum threshold;

a second rotary ring being associated with a second stop-electrode, so that the rotational movement of the second electrode will result in a rotational movement of the second stop-electrode, thereby allowing pre-setting of the boundary of the desired minimum vacuum level;

wherein the vacuum controller indicator has visual indicators;

wherein the first stop-electrode is electronically communicated with a first indicator, the second stop-electrode communicating with a second indicator.

23. An apparatus for surgical decompression and irrigation of a patient's bodily organ or cavity comprising:

a suction means including a first suction conduit fluidly communicating with a suction line of a catheter placed in the patient's organ or cavity;

a container for collecting material;

a second suction conduit fluidly communicating between the container and a suction source;

a vacuum sensor for detecting a level of negative pressure; and a vacuum controller-indicator, whereby when the vacuum is applied to the second conduit, a vacuum condition is generated in the second suction conduit and conveyed to the container which is hermetically isolated from ambient atmosphere and fluidly communicated with the second suction conduit, so that any pressure/vacuum change in the patient's organ or cavity or applied vacuum level will cause consequential changes in the pressure level in the first suction conduit, the container, and the second suction conduit;

wherein a vacuum change in either suction conduit or suction source or the reservoir communicates a signal to the vacuum controller-indicator so that the vacuum condition can be maintained in isolation from the vacuum source, thereby avoiding continuous operation of a pump motor connected to the vacuum source, wherein:

the second suction conduit has passageways communicating fluidly with the reservoir and the vacuum source;

the passageways having juxtaposed valves communicating with a valve controller;

the valve controller being in communication with a timer, the arrow and stop-cocks of the manometric device;

so that when the arrows moves axially under the influence of the vacuum in the suction means towards the first stop-electrode and when the vacuum magnitude in the suction means reaches a desired maximum cut-off vacuum level determined by the position of the first stop-electrode, the arrow contacts the first stop-electrode and in response to this contact, the first indicator is energized and the second indicator is energized;

whereupon the valve controller means and the timer are activated;

wherein the valve controller means closes the valves of the suction means and terminates fluid communication and thereby the vacuum communicated from the external vacuum source to the suction conduit means, so that despite termination of the external vacuum source the suction process is continued through vacuum suction conduits already generated in the receiver and an intrinsic vacuum condition is maintained as long as there are no pressure changes in the organ, reservoir and the passageways interconnected therewith.

24. An apparatus for surgical decompression and irrigation of a patient's bodily organ or cavity comprising:

a suction means including a first suction conduit fluidly communicating with a suction line of a catheter placed in the patient's organ or cavity;

a container for collecting material;

a second suction conduit fluidly communicating between the container and a suction source;

a vacuum sensor for detecting a level of negative pressure; and a vacuum controller-indicator, whereby when the vacuum is applied to the second conduit, a vacuum condition is generated in the second suction conduit and conveyed to the container which is hermetically isolated from ambient atmosphere and fluidly communicated with the second suction conduit, so that any pressure/vacuum change in the patient's organ or cavity or applied vacuum level will cause consequential changes in the pressure level in the first suction conduit, the container, and the second suction conduit;

wherein a vacuum change in either suction conduit or suction source or the reservoir communicates a signal to the vacuum controller-indicator so that the vacuum condition can be maintained in isolation from the vacuum source, thereby avoiding continuous operation of a pump motor connected to the vacuum source, wherein the second suction conduit has passageways communicating fluidly with the reservoir and the vacuum source;

the passageways having juxtaposed valves communicating with a valve controller;

the valve controller being in communication with a timer, the arrow and stop-electrodes of the manometric device;

so that when the vacuum condition in the suction means is relieved, the arrow moves towards the second stop-electrode; and when the vacuum value in the suction means reaches the desired minimum cut-off vacuum level determined by the position of the second stop-electrode, the arrow contacts the second stop-electrode, and in response to this contact, the first indicator is deactivated and the second indicator is energized; and the valves of the suction means are opened, thereby communicating the vacuum in the suction means from the external vacuum source.

25. The apparatus of claim 24, wherein the irrigation unit has an irrigation and air vent conduit with one directional flow from a fluid source toward the patient;

an irrigation conduit disposed between the fluid delivery source and the irrigation lumen of the catheter placed in the bodily organ or cavity;

wherein the irrigation conduit has juxtaposed first valves for regulating the fluid flow into the irrigation conduit and second valves for fluidly connecting the irrigation conduits with the ambient atmosphere;

wherein the valves are in communication with and operate in response to the valve controller;

wherein the valve controller is in communication with the timer and with the arrow and first and second stop-electrodes of the manometric device, so that when the arrow is moving towards the first stop-cock and contacts therewith, the valve controller and the timer are activated, and so that the valve controller immediately or after pre-set period of time opens the first and second valves optionally or after a certain period of time, thereby introducing the fluid, air or both into the irrigation conduit.

26. The apparatus of claim 24, wherein:

the irrigation unit has an irrigation and air vent conduit with one directional flow from a fluid source towards the patient;

an irrigation conduit disposed between the fluid delivery source and the irrigation lumen of the catheter placed in the bodily organ or cavity;

wherein the irrigation conduit has juxtaposed first valves for regulating fluid flow into the irrigation conduits with the ambient atmosphere;

wherein the valve controller is in communication with the timer and with the arrow and first and second stop-electrodes of the manometric device, so that when the arrow moves towards the second stop-electrode and contacts therewith, the valve controller and the timer are activated, so that the valve controller closes the said first and second valves optionally immediately or after a certain period of time, thereby terminating flow of fluid and air into the irrigation conduit.

27. The apparatus of claim 8 further comprising:

means for illumination located within the distal end of the tube, the means for illumination being in communication with the electrical supply means via the electrical lumen, so that when desired, the means for illumination may be energized and the distal tip of the tube may transilluminate through hollow viscus organs, thereby allowing the tube's position to be controlled and thereby facilitate positioning of the tube.

28. The apparatus of claim 8, wherein the electrical lumen in communication with the electrical supply means also communicates with a lamp located at the distal end of the tube.

29. The apparatus of claim 8, wherein the electrical lumen in communication with the electrical supply means also communicates with a pressure sensing device located at the distal end of the tube.

\* \* \* \* \*

UNITED STATES PATENT AND TRADEMARK OFFICE
CERTIFICATE OF CORRECTION

PATENT NO. : 5,512,045
DATED : April 30, 1996
INVENTOR(S) : Teimuraz P. Gurchumelidze It is certified that error appears in the above-indentified patent and that said Letters Patent is hereby corrected as shown below:

```
Column 3, line 25, delete "iS" and insert --is--.
Column 4, line 27, after "58" insert --(fluid flow)--.
Column 4, line 27, after "60" insert --(fluid flow)--.
Column 4, line 27, after "62" insert --(air vent)--.
Column 5, line 13, before "Insert" insert --1.--.
```

Signed and Sealed this

Twenty-seventh Day of January, 1998

BRUCE LEHMAN

Attest:

Attesting Officer

Commissioner of Patents and Trademarks